United States Patent [19]

Field et al.

[11] Patent Number: 4,560,692
[45] Date of Patent: Dec. 24, 1985

[54] 4-PIPERIDINO-2-PHENYLQUINOLINES

[75] Inventors: George F. Field, West Caldwell; William J. Zally, Cresskill, both of N.J.

[73] Assignee: Hoffmann-La Roche Inc., Nutley, N.J.

[21] Appl. No.: 631,971

[22] Filed: Jul. 18, 1984

[51] Int. Cl.[4] .................... A61K 31/47; C07D 215/16
[52] U.S. Cl. .................... 514/313; 546/159; 546/162; 560/44
[58] Field of Search ............... 424/258; 546/159, 162; 514/313

[56] References Cited

U.S. PATENT DOCUMENTS 4,299,835 11/1981 Champseix et al. ............... 546/152
4,402,961 9/1983 Dubroeucq et al. ............... 546/152
4,450,166 5/1984 Clemence et al. ............... 546/156

FOREIGN PATENT DOCUMENTS 1510009 12/1967 France .

OTHER PUBLICATIONS

A. Kar, Cinchophen Analogues as Potential CNS Agents, vol. 72, No. 9, 9/83.
Williams, Anxioselective Anxiolytics, 5/83, vol. 26, No. 5.
Arch, Pharm, (Weinheim) 316, 767–772, New Quinolines as Potential CNS Agents.
Biggio and Costa, Benzodiazepine Recognition Site Ligands: Biochemistry and Pharmacology, pp. 129–137.

Primary Examiner—Mark L. Berch
Assistant Examiner—Robert Benson
Attorney, Agent, or Firm—Jon S. Saxe; Bernard S. Leon; George M. Gould

[57] ABSTRACT

Disclosed are compounds of the formula

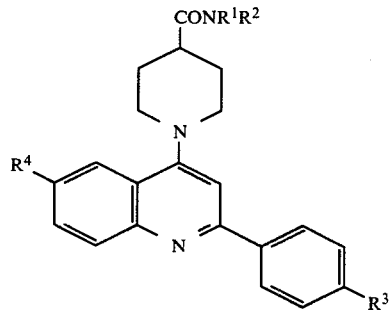

wherein:
$R^1$ and $R_2$ may be either the same or different and each is hydrogen or lower alkyl;
and wherein $R^3$ and $R^4$ may be either the same or different and each is hydrogen, halogen, or lower alkyl, with the proviso that $R^3$ and $R^4$ cannot both be hydrogen.

These compounds are useful as anticonvulsant or anxiolytic agents.

13 Claims, No Drawings

4-PIPERIDINO-2-PHENYLQUINOLINES

BACKGROUND OF THE INVENTION

1. Field of the Invention

The present invention concerns certain novel 4-amino-2-phenylquinolines, the synthesis of these compounds, and their use as anticonvulsant or anxiolytic agents.

2. Description of Related Art

The widespread interest of pharmaceutical chemists in the development of compounds which are useful as anxiolytic agents is shown in a recent review article by Williams [J. Med. Chem., 26, 619 (1983)]. In addition to describing the benzodiazepines, most notably chlordiazepoxide, diazepam, and oxazepam, this article also catalogs at least nine classes of non-benzodiazepines which have shown potential for use as anxiolytic agents. Of particular relevance to the present invention, PK 8165, a 2-phenylquinoline having the structure shown below, is mentioned as being a representative of one of these classes.

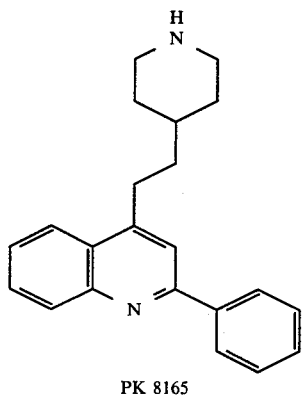

PK 8165

DESCRIPTION OF THE INVENTION

The present invention concerns compounds of the formula

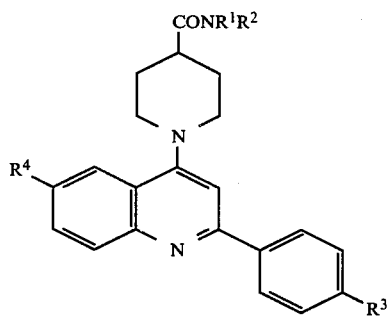

wherein $R^1$ and $R^2$ may be either the same or different and each is hydrogen or lower alkyl; and wherein $R^3$ and $R^4$ may be either the same of different and each is hydrogen, halogen, or lower alkyl, with the proviso that $R^3$ and $R^4$ cannot both be hydrogen.

Compounds of formula I have been found to be useful as anxiolytic agents.

As used herein, the term "lower alkyl" refers to both straight and branched chain hydrocarbon groups having 1 to 8 and preferably 1 to 4 carbon atoms, such as, for example, methyl, ethyl, propyl, isopropyl, tertiary butyl and the like.

As used herein, the terms "halogen" or "halo" refer to substituents which are derived from the halogen atoms fluorine, chlorine, bromine or iodine.

Within the context of the present invention, especially preferred lower alkyl groups are methyl and ethyl.

Also within the context of the invention, it is preferred that $R^3$ be selected from the group comprising Cl, Br, methyl and ethyl.

Preferred compounds of formula I are:

1-[2-(4-chlorophenyl)-4-quinolinyl]-N-ethyl-4-piperidinecarboxamide,

1-[2-(4-chlorophenyl)-6-fluoro-4-quinolinyl]-4-piperidine-carboxamide,

1-[2-(4-chlorophenyl)-4-quinolinyl]-N-methyl-4-piperi-dine-carboxamide, and

1-[2-(4-chlorophenyl)-4-quinolinyl]-4-piperidine-carboxamide.

The 4-amino-2-phenylquinolines of formula I can be manufactured through the use of two process variants which respectively comprise:

(a) reacting a 4-chloro-2-phenylquinoline of the formula

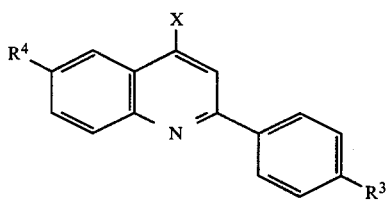

wherein $R^3$ and $R^4$ are as previously described and X is a halogen atom, with an isonipecotamide of the formula

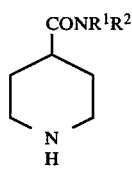

wherein $R^1$ and $R^2$ are as previously described or (b) initially reacting a compound of formula II, as previously described, with an isonipecotinic acid derivative of the formula

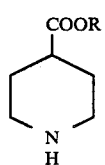

wherein R is lower alkyl, in order to yield an intermediate of the formula

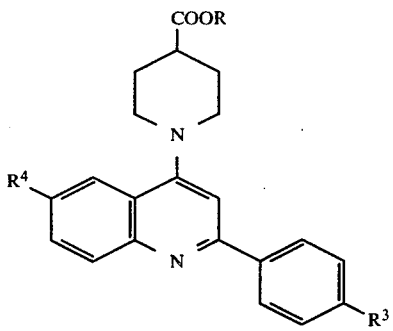

wherein R, R³ and R⁴ are as previously described, thereafter hydrolyzing this intermediate to yield a further intermediate of the formula

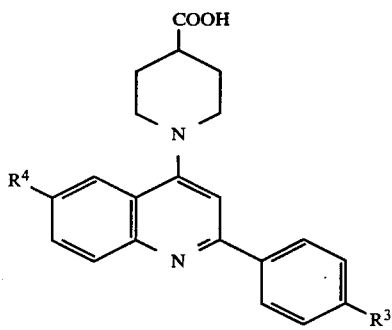

wherein R³ and R⁴ are as previously described, thereafter reacting the carboxylic acid intermediate of formula VI with a halogenating agent to yield a final intermediate of the formula

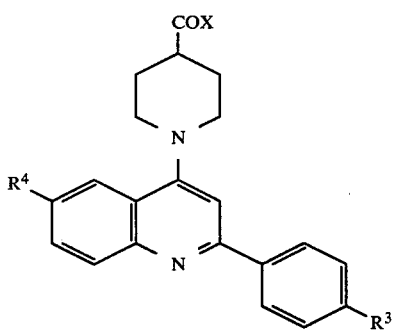

wherein R³ and R⁴ are as previously described and X is a halogen atom, and finally reacting this acid halide intermediate with and amine of the formula

NHR¹R²  VIII, wherein R¹ and R² are as previously described.

In connection with synthetic procedures set forth in this specification, it is to be noted that all temperatures are in degrees Celcius and all reactions are run at atmospheric pressure unless otherwise stated.

The reaction of a 4-halo-2-phenylquinoline of formula II with an isonipecotamide of formula III, which will either be a known compound or one which can be readily prepared using known procedures, in accordance with process variant (a) can be carried out in a known manner, either in the presence or absence of a solvent. Where used, appropriate solvents will be lower alkanols, phenols or other solvents known to be useful for nucleophilic exchange reactions such as dimethylformamide, dimethylsulfoxide and hexamethylphosphoramide. The reaction can be carried out at a temperature in the range between about 70° and 200° and preferably at about 150°. Particularly preferred as solvents are phenol and ethanol. Alternatively, where no solvent is used, the quinoline can be reacted with an excess of the isonipecotamide. This reaction takes place at a temperature in the range between about 100° and 180°.

The reaction of the quinoline of formula II with the isonipecotinate of formula IV, which will either be a known compound or one which can be readily prepared using known procedures, in accordance with process variant (b) can be carried out in lower alkanols or phenols as solvents at a temperature in the range between about 70° and 180°. It is preferred, however, to work without solvent at a temperature of about 150° to 170°.

Suitable bases for the hydrolysis of the intermediate of formula V are alkali metal hydroxides such as sodium hydroxide. The hydrolysis is carried out in water or lower alkanols at temperatures ranging between ambiant to about 150°. The acids of formula VI thus formed are precipitated from the reaction mixture by addition of an organic or mineral acid, such as acetic acid or hydrochloric acid, in an amount approximately equivalent to the amount of base used.

Suitable agents for converting the acid of formula VI to the acyl halides of formula VIII are thionyl chloride. phosphorus-oxychloride, phosphorus tribromide, and the like. The reaction is run in an inert solvent such as methylene chloride, chloroform, tetrahydrofuran, or the like, at a temperature in the range between about 30° and 150°. The use of methylene chloride at the boiling point of the reaction mixture is preferred.

Finally, the reaction of the acid chloride of formula VII with the amine of formula VIII, which will be either a known compound or one which can be readily prepared using known procedures, can be carried out in inert solvents such as chlorinated hydrocarbons, ethers or hydrocarbons, for example methylene chloride, tetrahydrofuran or toluene at a temperature in the range between about 0° and 100°, preferably at about 20°.

As should be readily apparent to persons skilled in the art other standard methods of conversion of esters or acids to amides may also be used to convert compounds of formula V or VI to compounds of formula I. For instance, treatment of a mixture of an acid of formula VI and a primary or secondary amine such as ethylamine in an inert solvent with a dehydrating agent such as dicyclohexylcarbodiimide can give an amide of formula I.

The 4-halo-2-phenylquinolines of formula II, many of which are novel, can be prepared in several ways.

Thus, for example, in instances wherein X is chlorine, these intermediates can be prepared as illustrated in Reaction Scheme 1, shown below, in which R³ and R⁴ are as previously described.

Reaction Scheme I

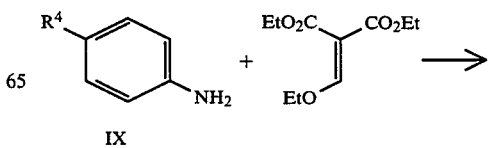

Reaction Scheme 1 -continued

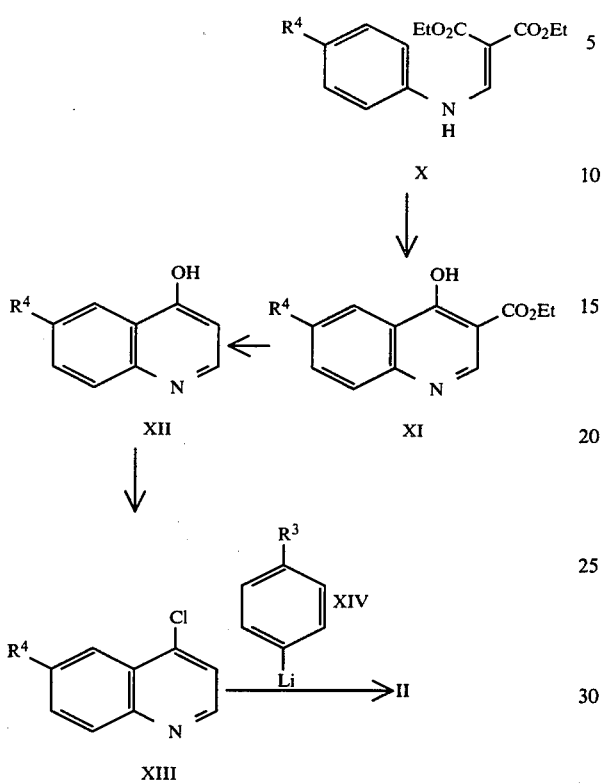

In connection with Reaction Scheme 1, the substituted aniline of formula IX will either be a known compound or one easily made using known procedures. The condensation of the aniline of formula IX with ethoxymethylenemalonate is accomplished in a known manner by heating a mixture of the components, either neat or in a solvent such as diphenyl ether or toluene, at a temperature of about 120°. The resulting intermediate of formula X is then cyclized in a conventional manner, for example by heating to a temperature of about 200° to 250°, in the presence of an inert organic solvent such as diphenyl ether.

The resulting quinoline of formula XI is decarboxylated in a conventional manner by first hydrolyzing the ester with a base, such as aqueous sodium hydroxide, at a temperature of, for example 100°, and then heating the resulting acid to a temperature of about 250°, either in an inert organic solvent, such as diphenyl ether, or without solvent.

The resulting 4-hydroxy quinoline of formula XII is treated in a known manner with a chlorinating agent, such as phosphorus oxychloride, to yield a 4-chloro compound of formula XIII.

Finally, the intermediate XIII is reacted in a known manner with an aryl lithium comound of formula XIV to yield the desired intermediate of formula II. This reaction can be carried out, for example, in an inert solvent such as diethyl ether or tetrahydrofuran, at a temperature in the range between about $-80°$ to $20°$ C. and under an inert atmosphere.

Reaction Scheme 2, below, illustrates another route to desired intermediates of formula II. Again $R^3$ and $R^4$, as used in this scheme, are as previously described.

Reaction Scheme 2

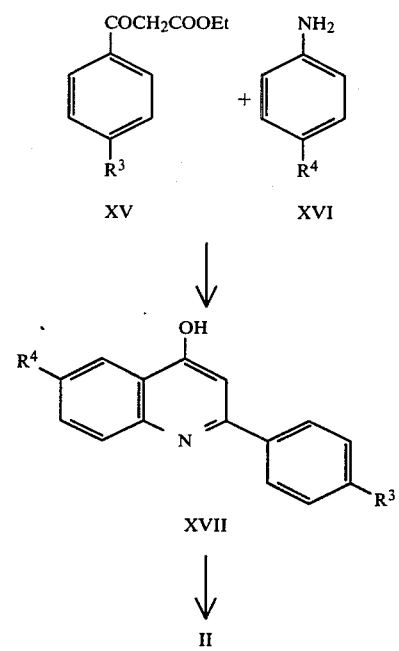

Referring to Reaction Scheme 2, both the benzoyl acetic acid ester of formula XV and the substituted aniline of formula XVI are known compounds or ones easily prepared using known methods.

The reaction of the compounds of formulae XV and XVI is accomplished in a known manner which comprises first condensing the two compounds, in the presence of an inert organic solvent such as toluene and a mild acid such as p-toluenesulfonic acid, under reflux. The product is concentrated in vacuo and then cyclized by heating at a temperature between about 200° and 260° in an inert organic solvent such as diphenyl ether, yielding the intermediate compound of formula XVII.

Reaction of the compound of formula XVII with a halogenating agent, such as phosphorus oxychloride or phosphorous tribromide, at reflux, optionally in an inert organic solvent such as diphenyl ether, yields the desired intermediate of formula II.

Yet another method for producing intermediates of formula II is shown in Reaction Scheme 3, below, wherein $R^3$ and $R^4$ are as previously described and $R^5$ is lower alkyl.

Reaction Scheme 3

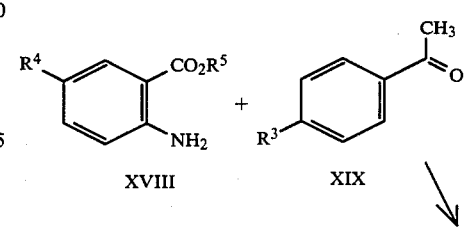

-continued
Reaction Scheme 3

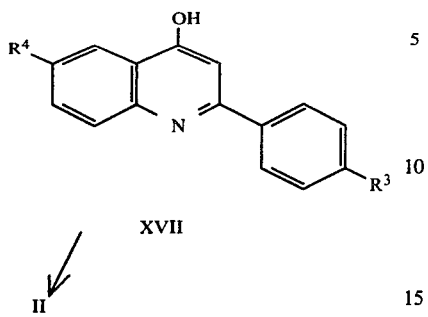

In connection with Reaction Scheme 3, both the anthranilic acid ester of formula XVIII and the substituted acetophenone of formula XIX will be known compounds or ones easily prepared using known methods.

This synthetic procedure initially entails the condensation of the compounds of formulae XVIII and XIX in the presence of a Lewis acid, such as aluminum chloride, in a high boiling solvent such as diphenyl ether, at reflux, yelding a compound of formula XVII. Further reaction to yield the desired compound of formula II is accomplished by treating the compound of formula XVII in a manner described in connection with Reaction Scheme 2.

A final method for producing compounds of formula II is illustrated by Reaction Scheme 4, below, in which $R^3$ and $R^4$ are as previously described and X is a halogen atom.

Reaction Scheme 4

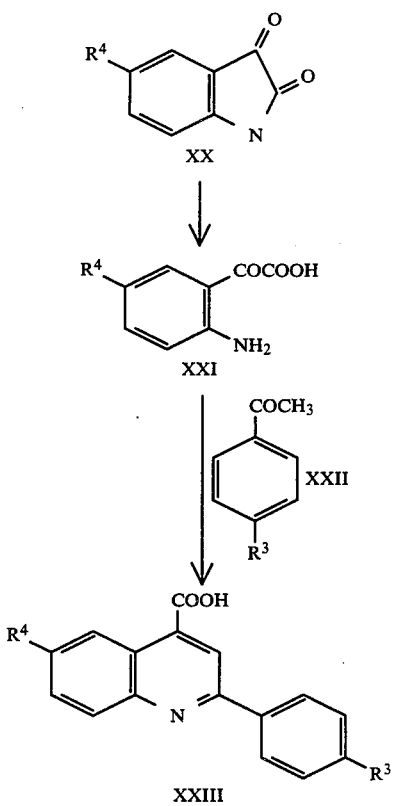

-continued
Reaction Scheme 4

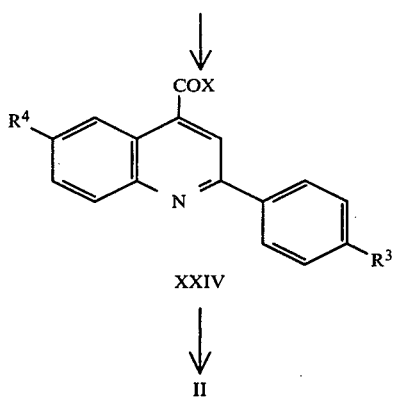

In connection with Reaction Scheme 4, it may be remarked that the substituted isatin of formula XX and the substituted acetophenone of formula XXII will be either known compounds or ones easily produced using known procedures.

The conversion of an isatin of formula XX to a intermediate compound of formula XXI proceeds in a conventional manner and entails treating the substituted isatin with a base such as, for example, sodium hydroxide in ethanol.

The condensation of the intermediate of formula XXI with the acetophenone of formula XXII also is a conventional reaction which may be carried out by refluxing the two reactants in a solvent such as ethanol, in the presence of a base such as sodium hydroxide.

The conversion of the acid of formula XXIII to the acid halide of formula XXIV is conventional and is accomplished through the treatment of the acid with a halogenating agent such as thionyl chloride or phosphorous tribromide, under reflux, in a inert organic solvent such as toluene.

Finally, the acid halide of formula XXIV is converted, in turn, to the desired 4-halo compound of formula II by decarbonylation using a standard agent such as, for example, a rhodium catalyst, at an elevated temperature.

The compounds of formula I provided by the instant invention are useful in the treatment of convulsive seizures or anxiety when incorporated into a suitable dosage form.

A suitable dosage for a compound of formula I would be in the range of about 10 to 500 mg. per day and, preferably, in the range of about 25 to 200 mg. per day in single or divided doses. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

The compounds of formula I may be administered as medicaments in the form of pharmaceutical preparations which contain them in association with a compatible pharmaceutical carrier material. Such carrier material can be an inert organic or inorganic carrier material suitable for parenteral or enteral administration, for example, oral administration. Examples of such carrier materials are water, gelatin, talc, starch, magnesium stearate, gum arabic, vegetable oils, polyalkyleneglycols, petroleum jelly and the like. The pharmaceutical preparations can be prepared in a conventional manner and finished dosage forms can be solid dosage forms, for example, tablets, dragees, suppositories, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservaties, stabilizers, emulsifiers, flavor-improvers, wetting agents, buffers, salts for varying the osmotic pressure and the like.

The following examples will further illustrate the invention:

EXAMPLE 1

Synthesis of 1-[2-(4-chlorophenyl)-4-quinolinyl]-N-ethyl-4-piperidinecarboxamide (a) 4-Chloro-2-(4-chlorophenyl)quinoline To a solution of 15.3 g (80 mmol) of 4-bromochlorobenzene in 100 ml of ether cooled to −25° was added 60 ml of a 1.6M solution of butyl lithium in hexane in three portions while maintaining the temperature below −20°. This mixture was allowed to warm to −5° during 15 min. It was then recooled to −20°, and a solution of 11.45 g (70 mmol) of 4-chloroquinoline in 40 ml of ether was added while maintaining the temperature at −20°. A yellow suspension formed. It was allowed to warm to 0° for 15 min, and was then stirred for a further 20 min at 0°–10°. To the reaction mixture was then added 20 ml of water and 20 g of iodine. After 20 min of stirring 40 ml of 3N sodium hydroxide solution was added and stirring was continued for a further 15 min. This mixture was then cooled to 10°, and the solid collected to give 17.65 g of product, mp 119°–122°.

(b) 1-[2-(4-Chlorophenyl)-4-quinolinyl]-4-piperidinecarboxylic acid ethyl ester

A mixture of 10 g (36.4 mmol) of 4-chloro-2-(4-chlorophenyl)quinoline, and 20 ml of ethyl isonipecotate was stirred and heated at 160°–170° for 2 hr. It was then cooled and diluted with 200 ml of water and 5 ml of ethanol. The solid which formed was collected, and recrystallized from ethanol to give 5.5 g of product ester, mp 124°–126°.

(c) 1-[2-(4-chlorophenyl)-4-quinolinyl]-4-piperidinecarboxylic acid

A mixture of 1.5 g (3.8 mmol) of 1-[2-(4-chlorophenyl)-4-quinolinyl]-4-piperidinecarboxylic acid ethyl ester, 2.7 ml of 3N aqueous sodium hydroxide, and 50 ml of ethanol was heated on a steam bath for 0.5 hr. It was then cooled, acidified with acetic acid, and diluted with water to give 1.4 g of product, mp 245°–247°.

(d) 1-[2-(4-Chlorophenyl)-4-quinolinyl]-4-piperidinecarbonyl chloride

A mixture of 8.0 g of the acid prepared above, 24 ml of thionyl chloride, and 400 ml of methylene chloride was stirred and heated under reflux for 1 hr. This reaction mixture was then concentrated in vacuo, and the residue collected with ether to 8.0 g of the acid chloride as a yellow solid.

(e) 1-[2-(4-Chlorophenyl)-4-quinolinyl]-N-ethyl-4-piperidinecarboxamide

To a solution of 100 ml of methylene chloride saturated at about 10° with ethylamine was added 2.0 g of 1-[2-4(4-chlorophenyl-4-quiolinyl]-4-piperidiecarbonyl chloride with stirring. This reaction mixture was stirred at room temperature for 1 hr. Then it was washed with 3×500 ml of water, dried over sodium sulfate, and concentrated in vacuo. The residue was crystallized from ether to give 1.3 g of white needles, mp 231°–233°.

EXAMPLE 2

Alternative synthesis of the intermediate 4-chloro-2(4-chlorophenyl)quinoline (a) 2-(4-chlorophenyl)-4-quinolinol To a stirred mixture of 16.52 g (0.1 mol) of ethyl o-aminobenzoate, 15.46 g (0.1 mol) of p-choroacetophenone, and 250 ml of diphenyl ether was carefully added 18.67 g of aluminum chloride. This mixture was heated under reflux for 2 hr and then let cool to 60° C. The solids were collected and washed with 2×100 ml of toluene. These solids were triturated twice with a mixture of 500 ml of 6N hydrochloric acid and 50 ml of acetone. Each time the solids were collected they were washed with 100 ml of 6N hydrochloric acid, 3×100 ml of water, and 2×50 ml of acetone. There was obtained 22.34 g of the above-named product, mp 327–330.

(b) 4-chloro-2-(4-chlorophenyl)quinoline.

A mixture of 21.6 g of 2-(4-chlorophenyl)-4-quinolinol and 46 ml of phosphorus oxychloride was heated under reflux for 45 min., cooled to room temperature, and poured carefully onto 750 ml of ice water. This mixture was neutralized with 146 ml of 50% sodium hydroxide and extracted with 600 ml of methylene chloride in three portions. The extracts were combined, filtered through 15 g of Florisil, and concentrated in vacuo to leave 19.35 g of the above-named compound.

EXAMPLE 3

Synthesis of 1-[2-(4-Chlorophenyl)-4-quinolinyl]-N,N-diethyl-4-piperidinecarboxamide In a manner analogous to that of Example 1(e), but using diethyamine instead of ethylamine, the above-named compound was prepared. mp 155°–157° dec. from ethanol.

EXAMPLE 4

Synthesis of 1-[2-(4-Chlorophenyl)-6-fluoro-4-quinolinyl]-4-piperidinecarboxamide (a) 2-(4-Chlorophenyl)-6-fluoro-4-hydroxyquinoline A mixture of 140 g (0.617 mol) of ethyl 4-chlorobenzoylacetate, 500 ml of toluene, 59 ml (0.621 mole) of 4-fluoroaniline, and 3 g of p-toluenesulfonic acid was stirred and heated under reflux for 4 hr. The reaction mixture was then concentrated in vacuo to leave 187 g of residue. This residue, dissolved in 75 ml of diphenyl either, was added to 500 ml of diphenyl ether stirred and heated to 245° in one portion. The reaction mixture was allowed to cool to 40°, and then diluted with hexane. The solid was collected and washed with methylene chloride to give 56 g of crude product, mp >350°.

(b) 4-Chloro-2-(4-chlorophenyl)-6-fluoroquinoline

A mixture of 25 g (91 mmol) of 2-(4-chlorophenyl)-6-fluoro-4-hydroxyquinoline and 50 ml of phosphorus oxychloride was stirred and heated under reflux for 2 hr. It was then cooled, poured onto ice and diluted with 500 ml of methylene chloride. This mixture was then made alkaline with 3N sodium hydroxide. The organic phase was separated, and the aqueous phase was extracted with 2×200 ml of methylene chloride. The organic extracts were combined, washed with water and with brine, dried over sodium sulfate, and concentrated in vacuo. The residue was collected and washed with hexane to give 22.2 g of product as a brownish solid, mp 169°–172°.

(c) 1-[2(4-Chlorophenyl)-6-fluoro 4-quinolinyl]-4-piperidinecarboxamide

A mixture of 4.4 g (15 mmol) of 4-chloro-2-(4-chlorophenyl)-6-fluoroquinoline, 3.9 g (30 mmol) of isonipecotamide, and 6 g of phenol was stirred and heated in an oil bath at 165°–180° for 2 hr. It was then cooled and diluted with 100 ml of water. Crystallization was induced by scratching. The solid was collected and washed with ether to give 5.2 g of crude product, mp 258°–260° dec. Recrystallization from pyridine/water gave off-white needles, mp 259°–261°.

EXAMPLE 5

Synthesis of 1-[2-(4-quinolinyl]-N-methyl-4-piperidinecarboxamide

To a solution of 100 ml of methylene chloride saturated at about 10° C. with methylamine was added 2.0 g of the acid chloride prepared in Example 1(d) with stirring. This reaction mixture was stirred at room temperature for 1 hr. Then it was diluted with 50 ml of water. The solid which formed at the interface was collected and dried to give 1.3 g of product as off-white needles, mp 250°–254°, and concentrated in vacuo. Recrystallization from ethanol gave white needles, mp 252–254.

EXAMPLE 6

Additional synthesis of 1-[2-(4-Chlorophenyl)-4-quinolinyl]-N-methyl-4-piperidinecarboxamide (a) N-methylisonipecotamide A mixture of 20 g (0.147 mol) of N-methylisonicotinamide, 100 ml of ethanol, and 1.2 g of platinum oxide was hydrogenated in a Parr shaker at 60° and 60 psi for 8 hr. The catalyst was filtered off, and the filtrate was concentrated in vacuo. The residue was crystallized from ether to give 20.5 g of crude product, mp 115°–121°.

(b) 1-[2-(4-Chlorophenyl)-4-quinolinyl]-N-methyl-4-piperidinecarboxamide

A mixture of 5.1 g (21 mmole) of 4-chloro-2-(4-chlorophenyl)quinoline, prepared as in Example 1(a), 6.2 g (42 mmole) of N-methylisonipecotamide, and 10 g of phenol was stirred and heated in an oil bath at 160° C. for 3.5 hr. It was then cooled and diluted with 100 ml of water. Crystallization was induced by scratching, warming and the addition of a small amount of ethanol. The solid was collected and washed with ether to give 7.0 g of crude product. Recrystallization from 150 ml of butanol gave 4.6 g of product, mp 251°–255° dec.

EXAMPLE 7

Synthesis of 1-[2-(4-chlorophenyl)-4-quinolinyl]-4-piperidinecarboxamide

In a manner analogous to that of Example 6, 4-chloro-2-(4-chlorophenyl)quinoline was reacted with isonipecotamide in phenol at 170° C., yielding the named compound, mp. 245°–247° dec., from ethanol.

EXAMPLE 8

Synthesis of 1-[2-(4-fluorophenyl)-4-quinolinyl]-4piperidinecarboxamide (a) 2-(4-fluorophenyl)-4-quinolinecarboxylic acid To a suspension of 36.78 g (0.25 mol) of isatin in 500 ml of ethanol was added 75 ml of 10N sodium hydroxide. After a few minutes of stirring a solid precipitated. To this mixture was added 35 ml (0.286 mol) of p-fluoroacetophenone, and it was stirred and heated under reflux for 1.5 hr. It was then allowed to cool slightly, and acidified with 250 ml of 3N hydrochloric acid. The precipitated solid was collected, washed with water and with ether, and dried to give 50.6 g of crude product, mp 205–215. Recrystallization from ethanol gave 38.8 g of the above-named acid, mp 210°–213° dec.

(b) 2-(4-fluorophenyl)-4-quinolinecarbonyl chloride

A mixture of 16.5 g of 2-(4-fluorophenyl-4-quinolinecarboxylic acid, 100 ml of thionyl chloride, and 50 ml of toluene was stirred and heated under reflux for 4 hr. The reaction mixture was the concentrated in vacuo, the residue was treated with more toluene, and the mixture again concentrated n vacuo. The residue was washed with ether to give 16 g of the above-named compound as a yellow solid.

(c) 4-Chloro-2-(4-fluorophenyl)quinoline

A mixture of 3 g of 2-(4-fluorophenyl)-4-quinolinecarbonyl chloride, and 0.1 g of tris(triphenylphosphine)rhodium(1) chloride was heated in an oil bath at 220°–235° for 40 min. The reaction mixture was cooled and extracted with methylene chloride. The extracts were filtered through 100 ml of silica gel and more methylene chloride was used to wash the silica. The filtrates were combined and concentrated in vacuo to leave 0.9 g of crude product, mp 90°–93°. Recrystallization from methanol gave an analytical sample, mp 91°–93°.

(d) 1-[2-(4-Fluorophenyl)-4-quinolinyl]-4-piperidinecarboxamide

A mixture of 1.44 g of 4-chloro-2-(4-fluorophenyl)-quinoline 1.3 g (10 mmol) of isonipecotamide, and 3 g of phenol was stirred and heated in an oil bath at 165°–170° for 4.5 hr. It was then cooled and diluted with water. It wa made alkaline with 3N sodium hydroxide, and crystallization was induced by the addition of ether and scratching. The solid was collected and washed with ether to give 1.6 g of crude product. Recrystallization from ethanol/water gave white needles (0.42g). mp 218°–220° dec.

EXAMPLE 9

Synthesis of 1-[6-Fluoro-2-phenyl-4-quinolinyl]-4-piperidinecarboxamide (a) 6-Fluoro-2-phenyl-4-quinolinol A mixture of 100 g of p-fluoroaniline, 160 ml of ethyl benzoylacetate, 200 ml of toluene, and 4 g of p-toluenesulfonic acid was stirred and heated under reflux with a Dean-Stark water trap until 15 ml of water was collected. The reaction mixture as then concentrated in vacuo to 275 g of a dark oil. This oil was poured into 500 ml of diphenyl ether heated to 240°. After 40 min the heat source was removed and the reaction mixture was allowed to cool to room temperature. It was then diluted with hexane and the solid collected. This solid was washed with hexane and with methylene chloride to give 104.3 g of 4-fluoro-2-phenyl-4-quinolinol, mp 298°–302°.

(b) 4-Chloro-6-fluoro-2-phenylquinoline

A mixture of 30.4 g (0.127 mol) of 6-fluoro-2-phenyl-4-quinolinol, and 65 ml of phosphorus oxychloride was stirred and heated under reflux for 2 hr. This mixture was concentrated in vacuo, diluted with methylene chloride, and poured onto ice. The aqueous phase was neutralized with 3N sodium hydroxide. The organic phase was separated, and the aqueous phase extracted with methylene chloride. The organic phases were combined, washed with water and with brine, dried over sodium sulfate, and concentrated in vacuo to leave 34.8 g of residue. This was dissolved in methylene chloride, and the solution filtered through a plug of alumina. Concentration of the filtrate left 23.7 g of 4-chloro-6-fluoro-2-phenylquinoline, mp 96°–99°.

(c) 1-(2-Phenyl-6-fluoro-4-quinolinyl)-4-piperidinecarboxamide

Reaction of 4-chloro-6-fluoro-2-phenylquinoline and isonipecotamide in a manner similar to that of Example 4(c) gave the named compound as off-white prisms, mp 230°–233°, after recrystallization from ethanol.

EXAMPLE 10

Synthesis of N-Ethyl-1-[6-fluoro-2-phenyl-4-quinolinyl]-4-piperidinecarboxamide (a) 1-[6-Fluoro-2-phenyl-4-quinolinyl]-4-piperidinecarboxylic acid ethyl ester A mixture of 9.0 g of 4-chloro-6-fluoro-2-phenylquinoline prepared according to the procedure described in example 9(b) and 18 ml of ethyl isonipecotate was stirred and heated in an oil bath at 160°–165° for 2 hr. It was then cooled and diluted with water. Addition of ethanol caused a solid to form which was collected to give 7.2 g of product as white prisms, mp 120°–124°.

(b) 1-[6-Fluoro-2-phenyl-4-quinolinyl]-4-piperidinecarboxylic acid

From 6.0 g of 1-[6-fluoro-2-phenyl-4-quinolinyl]-4-piperidinecarboxylic acid ethyl ester and 10 ml of 3N sodium hydroxide, treated in a manner similar to that described in Example 1C, there was obtained 5.6 g of product as yellow needles, mp 255°–260° dec.

(c) 1-[6-Fluoro-2-phenyl-4-quinolinyl]-4-piperidinecarbonyl chloride

A mixture of 4 g of 1-[6-fluoro-2-phenyl-4-quinolinyl]-4-piperidinecarboxylic acid, 12 ml of thionyl chloride, and 100 ml of methylene chloride were stirred and heated under reflux for 1 hr. The reaction mixture was cooled and concentrated in vacuo to leave 4.2 g of product as a yellow solid, mp 243°–5°.

(d) N-ethyl-1-[6-fluoro-2-phenyl-4-quinolinyl]-4-piperidinecarboxamide

In a manner analogous to that of Example 1(e) but using 1-[(6-fluoro-2-phenyl-4-quinolinyl]-4-piperidinecarbonyl chloride and ethylamine as starting materials the named compound was obtained as cream-colored needles, mp 225°–227° dec after recrystallization from methanol.

EXAMPLE 11

Synthesis of 1-[6-Fluoro-2-phenyl-4-quinolinyl]-N-propyl-4-piperidinecarboxamide In a manner analogous to that of Example 1(e) but using 1-[6-Fluoro-2-phenyl-4-quinolinyl]-4-piperidinecarbonyl chloride and propylamine as starting materials the named compound was obtained as off-white needles, mp 196°–198° dec. after recrystallization from methanol.

EXAMPLE 12

Synthesis of 1-[6-Fluoro-2-(4-fluorophenyl)-4-quinolinyl]-4-piperidinecarboxamide (a) 6-Fluoro-4-hydroxyquinoline A mixture of 216 ml of diethyl ethoxymethylenemalonate, 95 ml of 4-fluoroaniline, and 800 ml of diphenyl ether was stirred and slowly heated to 185° with distillation of the ethanol formed. The reaction mixture was then heated to 245° for 1.5 hr. The total amount of ethanol collected was 105 ml. The reaction mixture was allowed to cool to 60° at which time 250 ml of hexane was added. After it had stood overnight, the product was collected, washed with hexane and dried to give 223 g of solid mp 305°–309°.

A mixture of the above solid, 600 ml of 3N sodium hydroxide, and 250 ml of water was stirred and heated under reflux for 2 hr. To the hot brown cloudy mixture was slowly added 600 ml of 3N hydrochloric acid to precipitate the product, 6-fluoro-4-hydroxyquinoline-3-carboxylic acid. This product was filtered from the cooled reaction mixture.

This damp solid and 600 ml of diphenyl ether was slowly heated to 250° while water was allowed to distill out. The reaction mixture was held at this temperature for 20 min. and then allowed to cool to 100°. Then 500 ml of hexane was added, and the mixture was stirred for 1 hr. The product 6-fluoro-4-hydroxyquinoline, was collected and washed with hexane to give 144 g, mp 209°–212°.

(b) 4-Chloro-6-fluoroquinoline

A mixture of 52 g (0.319 mol) of 6-fluoro-4-hydroxyquinoline and 100 ml of phosphorus oxychloride was stirred and heated under reflux for 3 hr. The reaction mixture was concentrated in vacuo. A slurry of the residue in methylene chloride was poured into ice-water, and the mixture neutralized with 3N sodium hydroxide. The organic phase was separated, and the aqueous phase was extracted with 250 ml of methylene chloride twice. The organic phases were combined, washed with water, dired over sodium sulfate, and concentrated in vacuo. The residue was crystallized from hexane to give 27.95 g of product, mp 71°–74°.

(c) 4-Chloro-6-fluoro-2-(4-fluorophenyl)quinoline

To a solution of 4.37 g (25 mmol) of 1-bromo-4-fluorobenzene in 35 ml of ether cooled to −10° was added 15 ml of a 1.6M solution of butyl lithium in hexane in portions while maintaining the temperature below 0°. This mixture was stirred below 0° for 15 min. A solution of 3.63 g (20 mmol) of 4-chloro-6-fluoroquinoline in 20 ml of tetrahydrofuran was added while maintaining the temperature below 0°. The dark solution was stirred at room temperature for 20 min. To the reaction mixture was then added 5 ml of water and 5 g of iodine, and 10 ml of 3N sodium hydroxide. After 10 min of stirring the solid was collected to give 2.8 g of product, mp 130°–133°.

(d) 1-[6-fluoro-2-(4-fluorophenyl)-4-quinolinyl]-4-piperidinecarboxamide

The named compound was made in a manner analogous to that of Example 4(c) using 4-chloro-6-fluoro-2-

(4-fluoro-phenyl)quinoline and isonipecotamide as starting materials.

The named product was obtained as off-white needles, mp 244°–246° dec on recrystallization from ethanol.

EXAMPLE 13

Synthesis of 1-6-Fluoro-2-(4-fluorophenyl)-4-quinolinyl)]-N-methyl-4-piperidinecarboxamide The named compound was made in a manner analogous to that of Example 4(c) using 4-chloro-6-fluoro-2-(4-fluorophenyl)quinoline, prepared as described in Example 12(c) and N-methylisonipecotamide as starting materials. It was obtained as white prisms, mp 256°–259° on recrystallization from acetonitrile.

EXAMPLE 14

Synthesis of N-Ethyl-1-[6-fluoro-2-(4-fluorophenyl)-4-]piperidinecarboxamide

In a manner analogous to that of Example 1 the named compound was prepared using 1-[6-fluoro-2-phenyl-4-quinolinyl]-4-piperidinecarbonyl chloride, prepared as in Example 10(c), and ethylamine as starting materials. The named compound was obtained as white prisms, mp 236°–239° after recrystallization from ethanol.

EXAMPLE 15

Synthesis of 1-[2-(4-methylphenyl)-4-quinolinyl]-4-piperidinecarboxamide (a) 4-Chloro-2-(4-methylphenyl)quinoline To a solution of 4.3 g (25 mmol) of p-bromotoluene in 75 ml of ether cooled to 5° was dropwise added 15 ml of a 1.6M solution of butyl lithium in hexane, while maintaining the temperature below 5°. This mixture was stirred at 5° for 10 min. and at 30° for 10 min., and then cooled to −20°. A solution of 3.4 g (20 mmol) of 4-chloroquinoline in 15 ml of ether was added while maintaining the temperature at −20°. It was allowed to warm to room temperature during 15 min. To the reaction mixture was then added 10 ml of water and 5 g of iodine, and 60 ml of 3N sodium hydroxide. After 20 min. of stirring the organic layer was separated. The aqueous phase was extracted with an equal volume of ether in three portions. The organic phases were combined, washed with water, dried over sodium sulfate, and concentrated in vacuo to leave an oil. This oil was dissolved in methylene chloride and the solution filtered through a plug of alumina. The filtrate was concentrated in vacuo to give 2.6 g of product mp 75°–77°, as off-white needles.

(b) 1-[2-(4-methylphenyl)-4-quinolinyl]-4-piperidinecarboxamide

In a manner analogous to that of Example 1(b), but using 4-chloro-2-(4-methylphenyl)quinoline and isonipecotamide as starting materials, the named product was produced, mp. 230°–232° on recrystallization from acetonitrile.

EXAMPLE 16

Synthesis of 1-[2-(4-Bromophenyl)-4-quinolinyl]-4-piperidinecarboxamide (a) 2-(4-bromophenyl)-4-quinolinecarboxylic acid Treatment of 29.4 g of isatin, 47.8 g of p-bromoacetophenone, 60 ml of 10N sodium hydroxide in 400 ml of ethanol, according to the procedure of Example 8(a) without recrystallization gave 62.5 g of 2-(4-bromophenyl)-4-quinolinecarboxylic acid, mp 238°–240° dec. as off-white prisms.

(b) 2-(4-bromophenyl)-4-quinolinecarbonyl chloride

From 20 g of 2-(4-bromphenyl)-4-quinolinecarboxylic acid treated according to the procedure of Example 8(b) there was obtained 16 g of 2-(4-bromophenyl)-4-quinolinecarbonyl chloride, mp 139°–142° dec. as yellow prisms.

(c) 2-(4-Bromophenyl)-4-chloroquinoline

Treatment of 3 g of 2-(4-bromphenyl)-4-quinolinecarbonyl chloride, according to the procedure of Example 8(c) gave 2.2 g of 2-(4-bromophenyl)-4-chloroquinoline, mp 115°–117° dec. after filtration of a methylene chloride solution through alumina.

(d) 1-[2-(4-Bromophenyl)-4-quinolinyl]-4-piperidinecarboxamide

The named compound was made in a manner analogous to that of Example 8(d) using (2-(4-bromophenyl)-4-chloroquinoline and isonipecotamide as starting materials. It was obtained as white needles, mp 247°–249° dec on recrystallization from ethanol.

EXAMPLE 17

Synthesis of 1-[6-Fluoro-2-(4-methylphenyl)-4-quinolinyl]-4-piperidinecarboxamide (a) 4-Chloro-6-fluoro-2-(4-methylphenyl)quinoline To a solution of 4.3 g (25 mmol) of p-bromotoluene in 75 ml of ether cooled to 5° was dropwise added 10 ml of a 1.6M solution of butyl lithium in hexane, while maintaining the temperature below 5°. This mixture was stirred at 5° for 10 min and at 30° for 10 min. and then cooled to −20°. A solution of 3.63 g (20 mmol) of 4-chloro-6-fluoroquinoline, produced as in Example 12(b), in 20 ml of ether was added while maintaining the temperature at −20°. It was then allowed to stir at room temperature for 15 min. To the reaction mixture was then added 10 ml of water and 5 g of iodine, and 60 ml of 3N sodium hydroxide. After 20 min of stirring the organic layer was separated. The aqueous phase was extracted with an equal volume of ether. The organic phases were combined, washed with water, dried over sodium sulfate, and concentrated in vacuo to leave 5.8 g of crude product as a pale orange oil.

(b) 1-[6-Fluoro-2-(4-methylphenyl)-4-quinolinyl]-4-piperidinecarboxamide

The named compound was made in a manner analogous to that of Example 4(c) using 4-Chloro-6-fluoro-2-(4-methylphenyl)quinoline and isonipecotamide as starting materials. It was obtained as white needles, mp 246°–249° dec on recrystallization from pyridine.

EXAMPLE 18

Synthesis of
1-[6-Chloro-2-(4-methylphenyl)-4-quinolinyl]-4-piperidinecarboxamide (a) 6-chloro-2-(4-methylphenyl)-4-quinolinecarboxylic acid To a suspension of 18.15 g of 5-chloroisatin in 200 ml of ethanol was added 30 ml of 10N sodium hydroxide. To this mixture was added 16 ml (0.12 mol) of p-methylacetophenone, and it was stirred and heated under reflux for 3.2 hr. It was then concentrated in vacuo, and the residue was diluted to 250 ml with water. The above named acid was precipitated by the addition of acetic acid as a tan solid. Recrystallization from acetonitrile gave 31.6 g of the above-named acid as a tan solid.

(b) 6-chloro-2-(4-methylphenyl)-4-quinolinecarbonyl chloride

A mixture of 28.4 g of 6-chloro-2-(4-methylphenyl)-4-quinolinecarboxylic acid, 100 ml of thionyl chloride, and 200 ml of toluene was stirred and heated under reflux for 1.5 hr. The reaction mixture was then concentrated in vacuo, the residue was treated with more toluene, and the mixture again concentrated in vacuo. The residue was recrystallized from 300 ml of heptane to give 17.7 g of the above-named compound as a yellow solid.

(c) 4,6-Dichloro-2-(4-methylphenyl)quinoline

A mixture of 3 g of 6-chloro-2-(4-methylphenyl)-4-quinoline carbonyl chloride, and 0.2 g of tris(triphenylphosphine)rhodium(1) chloride was heated in an oil bath at 180°-200° for 40 min. The reaction mixture was cooled and extracted with methylene chloride. The extracts were filtered through 75 ml of alumina, and more methylene chloride was used to wash the alumina. The filtrates were combined and concentrated in vacuo to leave 0.8 g of crude product, mp 123°-125°.

(d) 1-[6-chloro-2-(4-methylphenyl)-4-quinolinyl]-4-piperidinecarboxamide

A mixture of 2.02 g (7 mmol) of 4,6-dichloro-2-(4-methylphenyl)quinoline, 1.6 g (12 mmol) of isonipecotamide, 5 g of phenol, and small amounts of sodium iodide and copper powder were stirred and heated at 160° for 4 hr. The reaction mixture was then diluted to 50 ml with water and made alkaline by the addition of concentrated ammonium hydroxide. The addition of ethyl acetate and ether induced the crystallization of 2.7 g of crude damp product. mp 260°-265°. The above-named compound was obtained as white needles, mp 265°-267° dec on recrystallization from ethanol.

EXAMPLE 19

Synthesis of
1-[6-Fluoro-2-(4-chlorophenyl)-4-quinolinyl]-N-methyl-4-piperidinecarboxamide The named compound was made in a manner analogous to that of Example 4(c) using 4-chloro-2-(4-chlorophenyl)-6-fluoroquinoline, prepared as described in Example 4(b), and N-methylisonipecotamide as starting materials. It was obtained as colorless needles, mp 279°-282°dec on recrystallization from pyridine.

EXAMPLE 20

Synthesis of
1-[6-Chloro-2-(4-fluorophenyl)-4-quinolinyl]-4-piperidinecarboxamide (a) 6-Chloro-4-hydroxyquinoline-3-carboxylic acid ethyl ester From a mixture of 216 g of diethyl ethoxymethylenemalonate, 126.6 g of p-chloroaniline, and 800 ml of diphenyl heated first at 150°-160° for 15 min and then at 245° for 20 min there was obtained on cooling the above-named compound as a precipitate. This precipitate was collected, and washed with water and with hexane to give 245 g of crude damp solid, which was used directly in the hydrolysis reaction described below.

(b) 6-Chloro-4-hydroxyquinoline

From 6-chloro-4-hydroxyquinoline-3-carboxylic acid ethyl ester, reacted in a manner similar to that described in Example 12, there was obtained the above-named compound of mp 265°-268° after recrystallization from ethanol.

(c) 4,6-Dichloroquinoline

From 93.6 g of 6-chloro-4-hydoxyquinoline and 200 ml of phosphorus oxychloride reacted in a manner similar to that described in Example 2(b) there was obtained 63.6 g of the above named compound as white needles, mp 101°-104°.

(d) 4,6-Dichloro-2-(4-fluorophenyl)quinoline

To a solution of 5.5 ml (50 mmol) of 1-bromo-4-fluorobenzene in 70 ml of ether cooled to −40° was added 21 ml of a 2.4M solution of butyl lithium in hexane while maintaining the temperature below −15°. This mixture was stirred at −15° for 15 min. A solution of 7.42 g (40 mmol) of 4,6-dichloroquinoline in 40 ml of tetrahydrofuran was added while maintaining the temperature at −20°. It was allowed to warm to 0° during 15 min. To the reaction mixture was then added 10 ml of water and 10.16 g (40 mmol) of iodine, and 15 ml of 3N sodium hydroxide. After 10 min of stirring this mixture was then cooled to 5°, and the solid collected. This solid was dissolved in methylene chloride, and the solution filtered through a plug of alumina. The filtrate was concentrated in vacuo to leave a residue which was crystallized from ethyl acetate to give 5.7g of crude product, mp 150°-156°.

(e) 1-[6-chloro-2-(4-fluorophenyl)-4-quinolinyl]-4-piperidinecarboxamide

The named compound was made in a manner analogous to that of Example 4(c) using 4,6-dichloro-2-(4-fluorophenyl)quinoline and isonipecotamide as starting materials. It was obtained as white needles, mp 250°-252° dec on recrystallization from ethanol.

EXAMPLE 21

Synthesis of
1-[6-Chloro-2-(4-fluorophenyl)-4-quinolinyl]-N-methyl-4-piperidinecarboxamide The named compound was made in a manner analogous to that of Example 4(c) using 4,6-dichloro-2-(4-fluorophenyl)quinoline, prepared as in Example 20, and N-methylisonipecotamide as starting materials. It was obtained as off-white needles, mp 260°-265° dec on recrystallization from pyridine/water.

EXAMPLE 22

Synthesis of
1-[6-Chloro-2-(4-chlorophenyl)-4-quinolinyl)]-4-piperidinecarboxamide (a) 4,6-Dichloro-2-(4-chlorophenyl)quinoline To a solution of 4.78 g (25 mmol) of 1-bromo-4-chlorobenzene in 40 ml of ether cooled to −10° was added 15 ml of a 2.4M solution of butyl lithium in hexane while maintaining the temperature below 0°. This mixture was stirred at 0° for 15 min. A solution of 3.96 g (20 mmol) of 4,6-dichloroquinoline, prepared as in Example 20(c), in 20 ml of tetrahydrofuran was added while maintaining the temperature of 0°. It was allowed to stir at 0° for 25 min. To the reaction mixture was then added 10 ml of water and 5 g of iodine, and 50 ml of 3N sodium hydroxide. After 10 min of stirring this mixture was then cooled to 5°, and the solid collected. This solid was washed with ether and dried to give 6.23 g of the above-named chloride, mp 204°–208°.

(b) 1-[6-chloro-2-(4-chlorophenyl)-4-quinolinyl]-4-piperidinecarboxamide

A mixture of 3.1 g of 4,6-dichloro-2-(4-chlorophenyl)quinoline, 2.56 g (20 mmol) of isonipecotamide, and 10 g of phenol was stirred and heated in an oil bath at 160°–170° for 4 hr. It was then cooled and diluted with water. It was made alkaline with 3N sodium hydroxide, and crystallization was induced by the addition of ether and scratching. The solid was collected and washed with ether to give 2.45 g of crude product. Recrystallization from ethanol gave the above-named compound as off-white prisms, mp 272°–275°.

EXAMPLE 23

Synthesis of
1-[6-Chloro-2-phenyl-4-quinolinyl]-4-piperidinecarboxamide (a) 6-Chloro-2-phenyl-7-quinolinol From 100 g of p-chloroaniline and 138.5 ml of ethyl benzoylacetate treated according to Example 4(a) there was obtained 115.6 g of 6-chloro-2-phenyl-4-quinolinol, mp greater than 350°.

(b) 4,6-dichloro-2-phenylquinoline

From 25.5 g of 6-chloro-2-phenyl-4-quinolinol and 50 ml of phosphorus oxychloride treated according to the procedure of Example 4(b) there was obtained 24.86 g of 4,6-dichloro-2-phenylquinoline, mp 114°–116°.

(c) 1-[6-chloro-2-phenyl-4-quinolinyl]-4-piperidinecarboxamide

The named compound was made in a manner analogous to that of Example 4(c) using 4,6-dichloro-2-(4-fluorophenyl)quinoline and isonipecotamide as starting materials. It was obtained as white needles, mp 253°–255° dec on recrystallization from ethanol.

EXAMPLE 24

Synthesis of
1-[6-Methyl-2-phenyl-4-quinolinyl]-4-piperidinecarboxamide (a) 4-Chloro-6-methyl-2-phenylquinoline This compound was made in a manner analogous to that of Example 4 using p-toluidine and ethyl benzoylacetate as starting materials. It was obtained as a light colored solid, mp 90°–93°.

(b) 1-[6-methyl-2-phenyl-4-quinolinyl]-4-piperidinecarboxamide

The named compound was made in a manner analogous to that of Example 4(c) using 4-chloro-6-methyl-2-phenylquinoline and isonipecotamide as starting materials. It was obtained as white solid, mp 245°–247° dec on recrystallization from pyridine.

EXAMPLE 25

Synthesis of
1-[2-(4-fluorophenyl)-6-methyl-4-quinolinyl]-4-piperidinecarboxamide (a) 4-chloro-6-methylquinoline This compound was made in a manner analogous to that of the synthesis of 4-chloro-6-fluoroquinoline described in Example 12. Starting from p-toluidine and diethyl ethoxymethylenemalonate the compound was obtained as a solid of mp 47°–51°.

(b) 4-chloro-2-(4-fluorophenyl)-6-methylquinoline

This compound was made in a manner analogous to that of the synthesis of 4,6-dichloro-2-(4-fluorophenyl)quinoline described in Example 20. From 3.5 ml of 1-bromo-4-fluorobenzene and 4.3 g of 4-chloro-6-methylquinoline there was obtained 2 g of the above named product as white solid, mp 93°–95°, after filtering a solution of the product in methylene chloride through a plug of silica gel.

(c) 1-[2-(4-Fluorophenyl)-6-methyl-4-quinolinyl]-4-piperidinecarboxamide

A mixture of 2.0 g of 4-chloro-2-(4-fluorophenyl)-6-methylquinoline, 1.88 g (10 mmol) of isonipecotamide, and 4 g of phenol was stirred and heated in an oil bath at 165°–170° for 2 hr. It was then cooled and diluted with water. Crystallization was induced by the addition of ethanol and scratching. The solid was collected and washed with ether to give 1.9 g of crude product, mp 264°–271° dec. Recrystallization from pyridine gave the titled product as off-white prisms, mp 275°–277° dec.

EXAMPLE 26

Synthesis of
1-[6-Methyl-2-(4-methylphenyl)-4-quinolinyl]-4-piperidinecarboxamide (a) 4-chloro-6-methyl-2-(4-methylphenyl)quinoline To a solution of 4.3 g (25 mmol) of p-bromotoluene in 50 ml of ether cooled to 5° was dropwise added 15 ml of a 1.6M solution of butyl lithium in hexane, while maintaining the temperature below 5°. This mixture was stirred at 5° for 10 min and at 30° for 10 min. and then cooled to −20°. A solution of 4.0 g (22 mmol) of 4-chloro-6-methylquinoline, prepared as in Example 25, in 20 ml of ether was added while maintaining the temperature at −20°. It was then allowed to stir at room temperature for 15 min. To the reaction mixture was then added 10 ml of water and 5 g of iodine, and 60 ml of 3N sodium hydroxide. After 20 min of stirring the organic layer was separated. The aqueous phase was extracted with an equal volume of ether. The organic phases were combined, washed with water, dried over sodium sulfate, and concentrated in vacuo to leave the above-named 4-chloroquinoline as a yellow oil. A solution of this oil in methylene chloride was filtered through a plug of alumina. The filtrate was concentrated in vacuo to give 3.22 g of the above-named product, mp 40°–50°.

(b) 1-[6-methyl-2-(4-methylphenyl)-4-quinolinyl]-4-piperidinecarboxamide

A mixture of 3.2 g of 4-chloro-6-methyl-2-(4-methylphenyl)quinoline, 3.06 g (24 mmol) of isonipecotamide, and 6 g of phenol was stirred and heated in an oil bath at 160° for 4 hr. It was then cooled and diluted with water. Crystallization was induced by the addition of ethanol and scratching. The solid was collected and washed with ether to give 3.18 g of crude product. Recrystallization from n-butanol gave off-white prisms, mp 242°–244° dec.

EXAMPLE 27

Synthesis of 1-[2-(4-Chlorophenyl)-6-methyl-4-quinolinyl]-4-piperidinecarboxamide (a) 4-chloro-2-(4-chlorophenyl)-6-methylquinoline The above named compound was prepared according to the procedure of Example 9 using p-toluidine and ethyl p-chlorobenzoylacetate as starting materials. It had mp 136°–138°.

(b) 1-[2-(4-chlorophenyl)-6-methyl-4-quinolinyl]-4-piperidinecarboxamide

A mixture of 10 g (35 mmol) of 4-chloro-2-(4-chlorophenyl)-6-methylquinoline, 8.9 g (70 mmol) of isonipecotamide, and 20 g of phenol was stirred and heated in an oil bath at 165°–170° for 3.5 hr. It was then cooled and diluted with water. Crystallization was induced by the addition of ethanol and scratching. The solid was collected and washed with ether to give 11.9 g of crude product. Recrystallization from pyridine gave the named compound as off-white prisms, mp 261°–265° dec.

EXAMPLE 28

Synthesis of 1-[2-(4-Chlorophenyl)-4-quinolinyl]-N,N-dimethyl-4-piperidinecarboxamide In a manner analogous to that of Example 1(e), but using dimethylamine rather than ethylamine, the above-named compound was prepared. mp 157°–159° dec. for ethanol.

EXAMPLE 29

Preparation of the starting material 4-(N-ethylcarbamoyl)piperidine (a) methyl isonicotinate A suspension of 100 g of isonicotinic acid (0.812 mol) in 250 ml of methanol was stirred and cooled to 10°. To this mixture was added dropwise 125 ml of sulfuric acid during 15 min. keeping the temperature below 20°. The reaction mixture was allowed to come to room temperature and then heated under reflux for 4.5 hr. After standing overnight it was poured onto 1 kg of ice and made alkaline with 235 g of sodium carbonate. The solid was filtered off, washed with water and with ether, and discarded. The filtrate was extracted with 3×300 ml of ether. The combined organic extracts were washed with water and with brine, dried over sodium sulfate, and concentrated in vacuo to leave 80 g (65%) of crude product as a pale oil.

(b) N-ethylisonicotinamide

A mixture of 200 ml of ethanol and 20 ml water was cooled in an ice bath and saturated with ethylamine for 0.5 hr. then 80 g of crude methyl isonicotinate was added with cooling. Ethylamine was again bubbled onto the reaction mixture for 10 min and then it was allowed to stand overnight at room temperature. It was then concentrated in vacuo to leave 82.82 g of a pale oil which became semisolid on cooling.

(c) (N-ethylcarbamoyl)piperidine

A solution of 82.8 g (0.551 mol) of N-ethylisonicotinamide in 600 ml of ethanol was hydrogenated over 5.0 g of platinum oxide at 60° C. and 200 psl for 5 hr. The reaction mixture was allowed to cool overnight, and the catalyst was filtered off. The filtrate was concentrated in vacuo. The residue was crystallized from ether to give 62.09 g of crude product.

EXAMPLE 30

In a manner analogous to that described in Example 29 the following starting materials were prepared:
a. 4-(N-methycarbamoyl)-piperidine
b. 4-(N-propylcarbamoyl-piperidine

EXAMPLE 31

Utilizing the procedures given below, the compounds of formula I synthesized in the previous examples were assayed for antimetrezol activity and $^3$H-diazepam binding activity. The 24 hour acute toxicity (LD-50, expressed as mg/kg) of each of these compounds was also determined in the standard fashion. The results of these assays are given in Table 1.

INTRAVENOUS ANTIPENTELENETETRAZOLE (Ptz.) TEST

Male CF-1 mice, 45–54 days old, housed in the same facility for one week and food-deprived for about 24 hours are used in this test. The test compound, dispersed in 5% acacia, is administered orally, initially, to three mice at 1/10 of the lethal dose ($LD_{50}$), as determined by prior testing. One hour later, Ptz. is administered intraveneously at 70 mg/kg (convulsant dose 100) and animals are observed 30 seconds for protection against convulsions. If the compound is active orally 8 animals are used per dose level. The dose (in mg/kg) at which 50% of the animals are protected from convulsive seizures is expressed as the $ED_{50}$. Calculations: The $ED_{50}$ values and 95% fiducial limits are calculated using a computer program based on the method of D. J. Finney ("Probit Analysis", Cambridge University Press, Cambridge, England, 1971).

Using this method, the activities for standard drugs are as follows:

| Drug | $ED_{50}$ (95% Fiducial Limits) |
| --- | --- |
| Chlordiazepoxide | 3.9(2.3–5.9) mg/kg |
| Diazepam | 1.0(0.69–1.6) mg/kg |
| Sodium Phenobarbital | 19(9.7–29) mg/kg |

$^3$H—Diazepam ($^3$H—Dz.) binding assay

Rat brain cortical fragments are prepared and the binding procedures performed as described by Mohler and Okada (Life Sciences, 20, 2101, 1977) except that Tris buffer is substituted for Krebs buffer. Drugs are assayed in triplicate. Radioactivity is measured by liquid scintillation counting. The results are expressed as the $IC_{50}$, which is the concentration of drug (in nanomoles/liter) required to inhibit $^3$H-Diazepam binding by 50%. Using this method, the activities for standard drugs are as follows:

| Drug | $IC_{50}$ |
| --- | --- |
| Diazepam | 5.0 nm/l |
| Flunitrazepam | 1.8 nm/l |

-continued

| Drug | $IC_{50}$ |
|------|-----------|
| Flurazepam | 15.6 nm/l |

TABLE I

| Compound of Formula I | Ptz. $ED_{50}$ (mg/kg) | $^3$H—Dz. $IC_{50}$ (nm/l) | $LD_{50}$ (mg/kg) |
|---|---|---|---|
| 1-[2-(4-Chlorophenyl)-4-quinolinyl]-N—ethyl-4-piperidinecarboxamide | 26 | 9.0 | >1000 |
| 1-[2-(4-Chlorophenyl-4-quinolinyl]-N,N—diethyl-piperidine-carboxamide | No Data | 500 | No Data |
| 1-[2-(4-Chlorophenyl)-6-fluoro-4-quinolinyl]-4-piperidinecarboxamide | 15 | 36.0 | >1000 |
| 1-[2-(4-Chlorophenyl)-4-quinolinyl]-N—methyl-4-piperidinecarboxamide | 9 | 19.5 | >1000 |
| 1-[2-(4-Chlorophenyl)-4-quinolinyl]-4-piperidine-carboxamide | 24 | 29.0 | >1000 |
| 1-[2-(4-Fluorophenyl)-4-quinolinyl]-4-piperidine-carboxamide | >100 | 1.1 | >1000 |
| 1-(6-Fluoro-2-phenyl1-4-quinolinyl)-4-piperidine-carboxamide | 120 | 3.6 | >1000 |
| N—Ethyl-1-(6-fluoro-2-phenyl1-4-quinolinyl)-4-piperidinecarboxamide | 58 | 2.8 | >1000 |
| 1-(6-Fluoro-2-phenyl-4-quinolinyl)-N—propyl-4-piperidinecarboxamide | >100 | 13.0 | >1000 |
| 1-[6-Fluoro-2-(4-fluorophenyl)-4-quinolinyl]-4-piperidinecarboxamide | 5 | 1.0 | >1000 |
| 1-[6-Fluoro-2-(4-fluorophenyl)-4-quinolinyl]-N—methyl piperidinecarboxamide | 13 | 1.8 | >1000 |
| 1-Ethyl-1-[6-fluoro-2-(4-fluorophenyl)-4-quinolinyl]-4-piperidinecarboxamide | 22 | 3.0 | >1000 |
| 1-[2-(4-methylphenyl)-4-quinolinyl]-4-piperidine-carboxamide | 37 | 1.7 | >1000 |
| 1-[2-(4-Bromophenyl)-4-quinolinyl]-4-piperidine-carboxamide | 41 | 35.0 | >1000 |
| 1-[6-Fluoro-2-(4-methyl-phenyl)-4-quinolinyl]-4-piperidinecarboxamide | 88 | 5.4 | >1000 |
| 1-[6-Chloro-2-(4-methyl-phenyl)-4-quinolinyl]-4-pipreidinecarboxamide | >100 | 60.0 | >1000 |
| 1-[2-(4-chlorophenyl)-6-fluoro-4-quinolinyl]-N—methyl-4-piperidinecarboxamide | >300 | 70.0 | >1000 |
| 1-[6-Chloro-2-(4-fluorophenyl)-4-quinolinyl]-4-piperidinecarboxamide | 29 | 28.0 | >1000 |
| 1-[6-Chloro-2-(4-fluorophenyl)-4-quinolinyl]-N—methyl-4-piperidine-carboxamide | 37 | 10.5 | >1000 |
| 1-[6-Chloro-2-(4-chloro-phenyl-4-quinolinyl-4-piperidinecarboxamide | No Data | 205.0 | No Data |
| 1-[6-Chloro-2-phenyl-4-quinolinyl)-4-piperidine-carboxamide | 50 | 96.0 | >1000 |
| 1-(6-Methyl-2-phenyl-4-quinolinyl)-4-piperidine-carboxamide | 90 | 28.0 | >1000 |
| 1-[2-(4-Fluorophenyl)-6-methyl-4-quinolinyl]-4-piperidinecarboxamide | >100 | 34.0 | >1000 |
| 1-[6-Methyl-2-(4-methyl- | No Data | 290.0 | No |

TABLE I-continued

| Compound of Formula I | Ptz. $ED_{50}$ (mg/kg) | $^3$H—Dz. $IC_{50}$ (nm/l) | $LD_{50}$ (mg/kg) |
|---|---|---|---|
| phenyl)-4-quinolinyl]-4-piperidinecarboxamide | | | Data |
| 1-[2-(4-Chlorophenyl)-6-methyl-4-quinolinyl]-4-piperidinecarboxamide | No Data | 460.0 | No Data |
| 1-[2-(4-Chlorophenyl)-4-quinolinyl]-N,N—dimethyl-4-piperidine-carboxamide | 24 | 80.0 | >1000 |

">" indicates that compound was not tested above indicated value.

EXAMPLE 32

The following various formulations can be prepared for compounds of formula I provided by the invention wherein the compound of formula I is selected from amongst 1-[2-(4-chlorophenyl)-4-quinolinyl]-N-ethyl-4-piperidinecarboxamide.

1-[2-(4-chlorophenyl)-6-fluoro-4-quinolinyl]-4-piperidinecarboxamide.

1-[2-(4-chlorophenyl)-4-quinolinyl]-N-methyl-4-piperidinecarboxamide.

1-[2-(4-chlorophenyl)-4-quinolinyl]-4-piperidinecarboxamide

(a) Direct Compression Tablet Formulation

| | mg/tablet | | | |
|---|---|---|---|---|
| (1) Compound of Formula I | 1.0 | 5.0 | 10.0 | 50.0 |
| (2) Lactose, Anhydrous DTG | 127.0 | 142.5 | 182.0 | 206.0 |
| (3) Microcrystalline Cellulose | 40.0 | 50.0 | 60.0 | 80.0 |
| (4) Modified Starch | 10.0 | 12.5 | 15.0 | 20.0 |
| (5) Cornstarch | 20.0 | 25.0 | 30.0 | 40.0 |
| (6) Magnesium Stearate | 2.0 | 2.5 | 3.0 | 4.0 |
| Total | 200 mg | 250 mg | 300 mg | 400 mg |

PROCEDURE (1) Mix Items 1–5 in a suitable mixer for 1 to 15 minutes.
(2) Add Item 6 and mix for 5 minutes. Compress on a suitable press.

(b) Capsule Formulation

| | mg/tablet | | | |
|---|---|---|---|---|
| (1) Compound of Formula I | 1.0 | 5.0 | 10.0 | 50.0 |
| (2) Lactose | 149.0 | 182.5 | 215.0 | 250.0 |
| (3) Cornstarch | 40.0 | 50.0 | 60.0 | 80.0 |
| (4) Magnesium Stearate | 2.0 | 2.5 | 3.0 | 4.0 |
| (5) Talc | 8.0 | 10.0 | 12.0 | 16.0 |
| Total | 200 mg | 250 mg | 300 mg | 400 mg |

PROCEDURE (1) Mix Items 1–3 in a suitable mixer. Mill through suitable mill.
(2) Mix with Items 4 and 5 and fill on capsule machine.

(c) Wet Granulation Tablet Formulation

| | mg/tablet | | | |
|---|---|---|---|---|
| (1) Compound of Formula I | 1.0 | 5.0 | 10.0 | 50.0 |
| (2) Lactose | 195.0 | 230.0 | 264.0 | 263.0 |
| (3) Pregelatinized Starch | 12.5 | 15.0 | 17.5 | 20.0 |
| (4) Cornstarch | 25.0 | 30.0 | 35.0 | 40.0 |
| (5) Modified Starch | 12.5 | 15.0 | 17.5 | 20.0 |

-continued

| (c) Wet Granulation Tablet Formulation | | | | |
|---|---|---|---|---|
| | | | mg/tablet | |
| (6) Magnesium Stearate | 4.0 | 5.0 | 6.0 | 7.0 |
| | Total | 200 mg | 300 mg | 350 mg | 400 mg |

PROCEDURE (1) Mix Items 1-5 in a suitable mixer, granulate with water. Dry overnight in an oven. Mill through a Fitzpatrick mill.

(2) Mix with Item 6 and compress on a suitable press.

We claim:

1. A compound of the formula

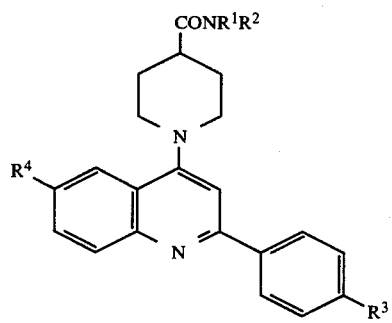

wherein:

$R^1$ and $R^2$ may be either the same or different and each is hydrogen or lower alkyl;

and wherein $R^3$ and $R^4$ may be either the same or different and each is hydrogen, halogen, or lower alkyl, with the proviso that $R^3$ and $R^4$ cannot both be hydrogen.

2. A compound of formula I, according to claim 1, wherein $R^1$ and $R^2$ are selected from the group consisting of a hydrogen, methyl and ethyl.

3. A compound of formula 1, according to claim 1, wherein $R^3$ is selected from the group consisting of Cl, Br, methyl and ethyl.

4. In accordance with claim 1, a compound which is a 1-[2-(4-halophenyl)-4-quinolinyl]-N-lower alkyl-4-piperidinecarboxamide.

5. In accordance with claim 4, the compound 1-[2-(4-chlorophenyl)-4-quinolinyl]-N-methyl-4-piperidine-carboxamide.

6. In accordance with claim 1, the compound 1-[2-(4-chlorophenyl)-6-fluoro-4-quinolinyl]-4-piperidinecarboxamide.

7. In accordance with claim 4, the compound 1-[2-(4-chlorophenyl)-4-quinolinyl]-N-ethyl-4-piperidinecarboxamide.

8. In accordance with claim 1, the compound 1-[2-(4-chlorophenyl)-4-quinolinyl]-4-piperidinecarboxamide.

9. A method for treating convulsive seizures or anxiety which comprises administering, to a host requiring such treatment, a therapeutically effective amount of a compound of the formula

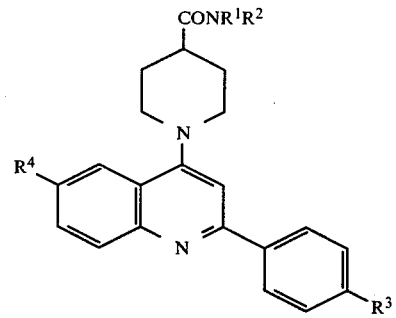

wherein:

$R^1$ and $R^2$ may be either the same or different and each is hydrogen or lower alkyl;

and wherein $R^3$ and $R^4$ may be either the same or different and each is hydrogen, halogen, or lower alkyl, with the proviso that $R^3$ and $R^4$ cannot both be hydrogen.

10. A pharmaceutical composition for the treatment of convulsive seizures or anxiety comprising a pharmaceutically acceptable carrier and an effective amount of a compound of the formula

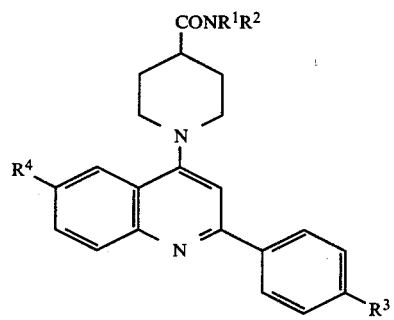

wherein:

$R^1$ and $R^2$ may be either the same or different and each is hydrogen or lower alkyl;

and wherein $R^3$ and $R^4$ may be either the same or different and each is hydrogen, halogen, or lower alkyl, with the proviso that $R^3$ and $R^4$ cannot both be hydrogen.

11. A compound of the formula

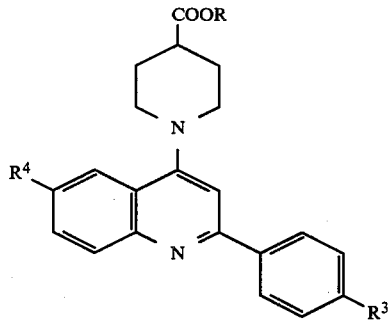

wherein R is lower alkyl and $R^3$ and $R^4$ may be either the same or different and each is hydrogen, halogen, or lower alkyl, with the proviso that $R^3$ and $R^4$ cannot both be hydrogen.

12. A compound of the formula

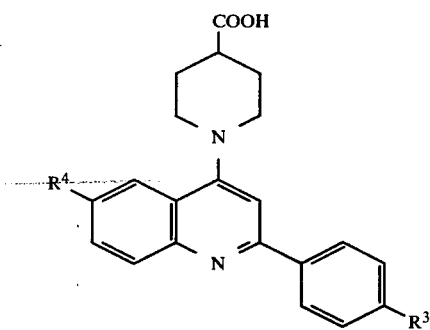

wherein $R^3$ and $R^4$ may be either the same or different and each is hydrogen, halogen, or lower alkyl, with the proviso that $R^3$ and $R^4$ cannot both be hydrogen.

13. A compound of the formula

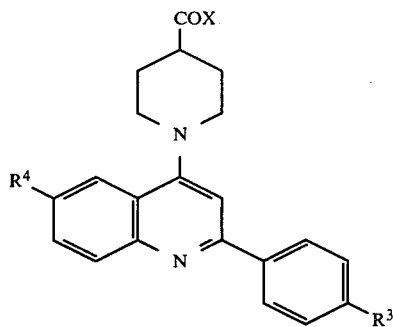

wherein X is a halogen atom and $R^3$ and $R^4$ may be either the same or different and each is hydrogen, halogen, or lower alkyl, with the proviso that $R^3$ and $R^4$ cannot both be hydrogen.

* * * * *